(12) United States Patent
Ishida

(10) Patent No.: US 9,874,842 B2
(45) Date of Patent: Jan. 23, 2018

(54) SHEET DETERMINATION APPARATUS USING ULTRASONIC WAVE TRANSMITTING UNIT OR RECEPTION UNIT

(71) Applicant: CANON KABUSHIKI KAISHA, Tokyo (JP)

(72) Inventor: Tsutomu Ishida, Suntou-gun (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 557 days.

(21) Appl. No.: 14/449,833

(22) Filed: Aug. 1, 2014

(65) Prior Publication Data

US 2015/0037053 A1  Feb. 5, 2015

(30) Foreign Application Priority Data

Aug. 5, 2013 (JP) ................................ 2013-162796
Jun. 27, 2014 (JP) ................................ 2014-133248
Jul. 31, 2014 (JP) ................................ 2014-155778

(51) Int. Cl.
*G01N 29/24* (2006.01)
*G03G 15/02* (2006.01)
*G03G 15/00* (2006.01)
*G01N 29/11* (2006.01)

(52) U.S. Cl.
CPC ......... *G03G 15/5029* (2013.01); *G01N 29/11* (2013.01); *G01N 29/2462* (2013.01);
(Continued)

(58) Field of Classification Search
CPC .............. G03G 15/5029; G01N 29/11; G01N 2291/0237; G01N 2291/044;
(Continued)

(56) References Cited

U.S. PATENT DOCUMENTS 3,262,307 A * 7/1966 Hart ..................... G01N 29/043
                                                                310/335
4,238,963 A * 12/1980 Ries ....................... G01H 3/005
                                                                 73/1.86

(Continued)

FOREIGN PATENT DOCUMENTS

| JP | 2001-351141 A | 12/2001 |
| JP | 2005-082350 A | 3/2005 |
| JP | 2005-350167 A | 12/2005 |
| JP | 2010-018432 | 1/2010 |

*Primary Examiner* — Laura Martin
*Assistant Examiner* — Rose M Miller
(74) *Attorney, Agent, or Firm* — Fitzpatrick, Cella, Harper & Scinto

(57) ABSTRACT

A protection member is arranged such that the distance from an opening plane of a reception guide to the center of the protection member is half of the distance from the opening plane of the reception guide to the surface of a reception vibration member. In other words, the arrangement position of the protection member is in the center between the opening plane of the reception guide and the surface of the reception vibration member. Accordingly, even if a protection member is arranged, a transmission coefficient is obtained that is equal to a transmission coefficient in the case where no protection member is present.

24 Claims, 12 Drawing Sheets

(52) U.S. Cl.
   CPC . *G01N 29/2468* (2013.01); *G01N 2291/0237* (2013.01); *G01N 2291/044* (2013.01); *G01N 2291/048* (2013.01); *G03G 2215/00324* (2013.01); *G03G 2215/00611* (2013.01)

(58) Field of Classification Search
   CPC ......... G01N 2291/048; G01N 29/2462; G01N 29/2468; G01N 29/2487; G01N 29/28; G01N 29/221; G10K 11/32; G10K 11/02; G10K 11/22; G10K 11/24
   USPC .................................. 73/632, 644, 617, 1.86
   See application file for complete search history.

(56) References Cited

U.S. PATENT DOCUMENTS

| | | | |
|---|---|---|---|
| 6,032,535 A * | 3/2000 | Fischer | B60G 17/01933 267/64.19 |
| 6,073,491 A * | 6/2000 | Fischer | F16F 9/05 267/64.19 |
| 6,993,967 B2 * | 2/2006 | Forgue | G01F 23/2968 73/1.82 |
| 7,331,578 B2 | 2/2008 | Sano et al. | |
| 8,256,294 B2 | 9/2012 | Ishida | |
| 2004/0011141 A1 * | 1/2004 | Lynnworth | G01F 1/667 73/861.27 |
| 2011/0142459 A1 * | 6/2011 | Aoki | G03G 15/6558 399/12 |

* cited by examiner

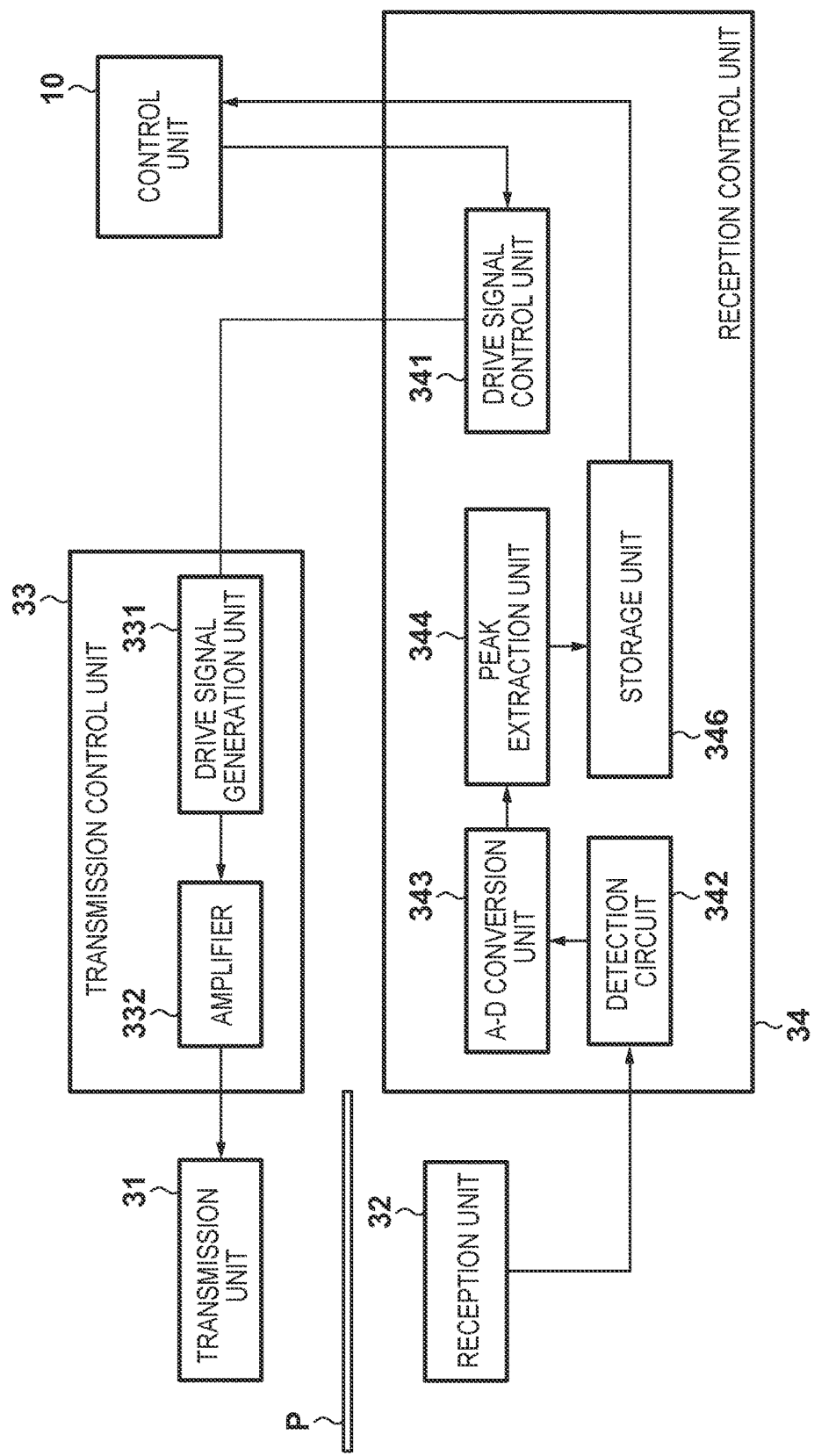

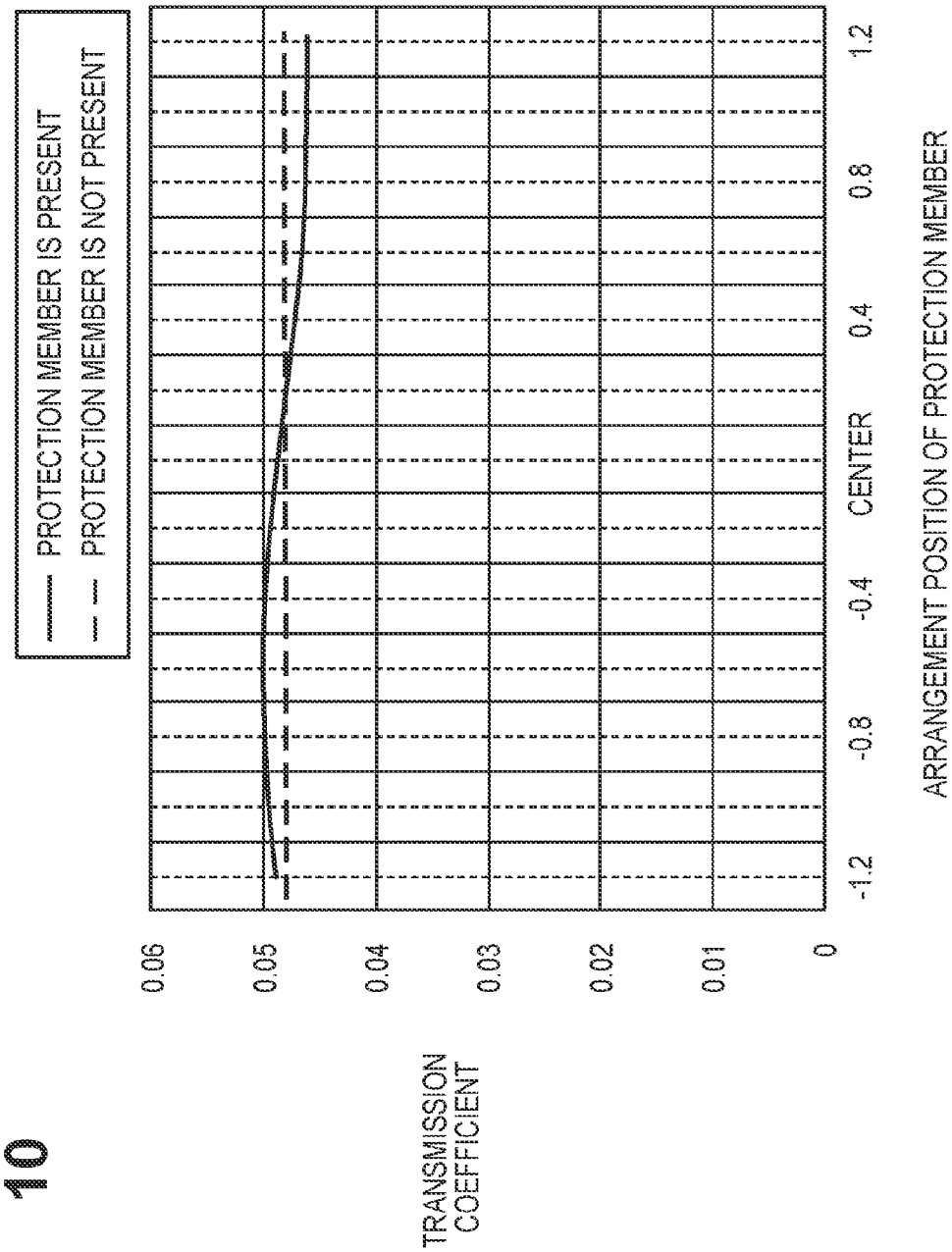
F I G. 10

SHEET DETERMINATION APPARATUS USING ULTRASONIC WAVE TRANSMITTING UNIT OR RECEPTION UNIT

BACKGROUND OF THE INVENTION

Field of the Invention

The present invention relates to an ultrasonic wave transmitting unit or reception unit, a sheet determination apparatus, and an image forming apparatus.

Description of the Related Art

Image forming apparatuses such as multi-function printers and laser printers use an ultrasonic wave sensor to determine the type of a sheet inside of the image forming apparatus and set image formation conditions such as transfer conditions and fixing conditions according to the determination result. Incidentally, there are cases where ultrasonic waves transmitted from a transmission unit are reflected multiple times and received by a reception unit. Reflection can occur due to a sheet, and also due to members in the periphery of the transmission unit and the reception unit, such as conveyance rollers and conveyance guides for conveying the sheet.

Japanese Patent Laid-Open No. 2001-351141 proposes attaching sonic wave guides by which sonic waves converge respectively at a wave transmitter and at a wave receiver. Japanese Patent Laid-Open No. 2010-018432 proposes determining the length of guides based on the wavelength of the ultrasonic waves so as to stabilize the output of ultrasonic waves that have passed through a recording medium.

Incidentally, there are cases where the ultrasonic wave sensor is arranged at a position at which a user can touch it with his or her fingers. Since an ultrasonic wave sensor transmits and receives ultrasonic waves due to a vibration member vibrating, if the vibration member is touched by a user, it cannot operate normally. Sometimes there are also cases where the ultrasonic wave sensor malfunctions.

SUMMARY OF THE INVENTION

In view of this, the present invention makes it difficult for a user to touch the vibrating member of at least one of a transmission unit and a reception unit for ultrasonic waves.

The present invention provides an ultrasonic wave transmission/generating unit comprising the following elements. A vibration member vibrates so as to transmit ultrasonic waves. A guide member guides ultrasonic waves transmitted from the vibration member. A protection member protects the vibration member and that is provided in the guide member, wherein in a direction on a line that passes through the center of the vibration member and is perpendicular to a surface on a side of the vibration member that transmits ultrasonic waves, a part of the vibration member overlaps the protection member.

The present invention also provides an ultrasonic wave reception unit comprising the following elements. A vibration member vibrates by receiving ultrasonic waves. A guide member guides ultrasonic waves to the vibration member. A protection member protects the vibration member and that is provided in the guide member, wherein in a direction on a line that passes through the center of the vibration member and is perpendicular to a surface on a side of the vibration member that receives ultrasonic waves, a part of the vibration member overlaps the protection member.

Further features of the present invention will become apparent from the following description of exemplary embodiments with reference to the attached drawings.

BRIEF DESCRIPTION OF THE DRAWINGS

FIG. 2 is a block diagram showing a control unit and an ultrasonic wave sensor that constitute a sheet determination apparatus.

FIG. 10 is a diagram showing the relationship between the arrangement position of a protection member and a transmission coefficient.

DESCRIPTION OF THE EMBODIMENTS

Hereinafter, embodiments of the invention will be described with reference to the drawings. It should be noted that the following embodiments are not intended to limit the invention recited in the claims, and all combinations of features described in the embodiments are not necessarily mandatory as solutions provided by the invention.

First Embodiment

Figure 1:
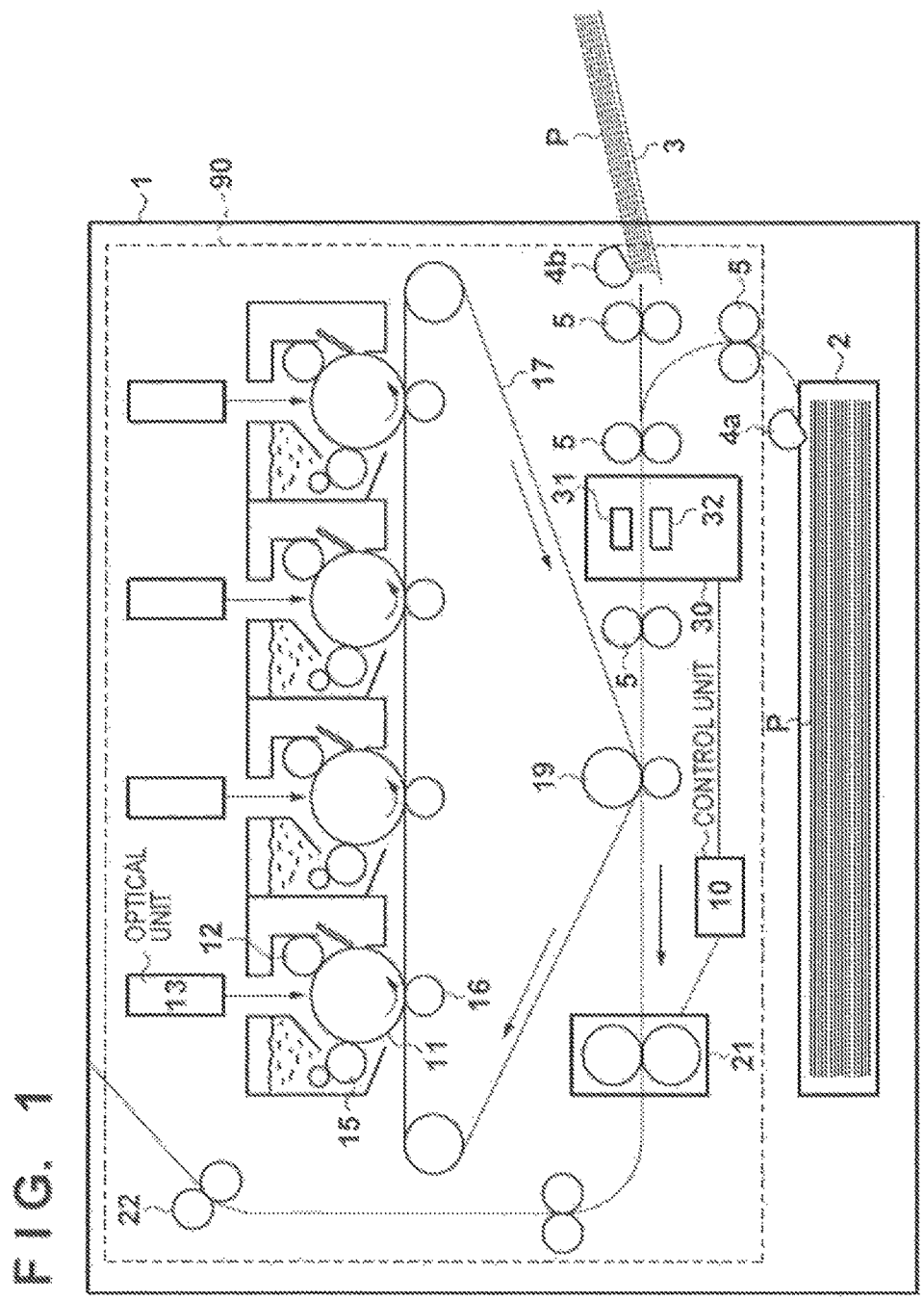
FIG. 1 is a diagram of an overall configuration of an image forming apparatus.

A sheet determination apparatus of the present embodiment can be used in an image forming apparatus such as a multi-function printer or a printer, for example. As an example of this, FIG. 1 shows an image forming apparatus 1 equipped with a sheet determination apparatus. In the image forming apparatus 1, multiple image forming units are arranged in a line, and toner images are transferred onto a sheet by an intermediate transfer member. In this example, the image forming units form an image using yellow, magenta, cyan, and black toner images respectively.

A sheet P is fed by feed rollers 4a and 4b that feed sheets from a feed cassette 2 or a feed tray 3. A conveyance roller 5 conveys the sheet P from the upstream side to the downstream side in the conveyance direction of the sheet P. An ultrasonic wave sensor 30 includes an ultrasonic wave transmission unit 31 and an ultrasonic wave reception unit 32 and detects ultrasonic waves corresponding to the type (grammage, thickness, etc.) of the sheet P. Based on the detection result of the ultrasonic wave sensor 30, a control unit 10 determines the type (grammage, thickness, etc.) of the sheet P and controls the fixing temperature of a fixing unit 21. The reason for this is because the appropriate fixing temperature varies depending on the grammage and thickness of the sheet P. Note that the control unit 10 may adjust the conveyance speed of the sheet P based on the determination result. This is to decrease the conveyance speed with a thick sheet relative to a thin sheet such that thermal energy applied to toner is increased. Note that the control unit 10 may adjust the voltage value that is to be supplied to a secondary transfer roller pair 19 based on the determination result. The reason for this is because the appropriate voltage value varies depending on the grammage and thickness of the sheet P. Here, the aforementioned processing was mentioned as an example of an image formation condition, but the invention is not limited to this, and any processing may be used as long as it is possible to perform control according to the grammage and thickness of the sheet P. In this way, the ultrasonic wave sensor 30 and the control unit 10 function as a sheet determination apparatus. Also, the control unit 10 functions as a determination unit for determining the type of sheet based on a detection signal output from an ultrasonic wave sensor. Also, the control unit 10 may skip the processing for determining the type of the sheet P and control the image formation conditions directly based on the output result of the ultrasonic wave sensor 30.

A photoreceptor drum 11 is uniformly charged at a predetermined potential by a charging unit 12. An optical unit 13 emits laser light that corresponds to image data to the uniformly-charged photoreceptor drum 11 and forms an electrostatic latent image. A developer 15 forms a toner image by using toner to develop the electrostatic latent image formed on the photoreceptor drum 11. A primary transfer roller 16 transfers the toner image from the photoreceptor drum 11 to the intermediate transfer belt 17. The secondary transfer roller pair 19 performs secondary transfer of the toner image formed on the intermediate transfer belt 17 onto the sheet P. The fixing unit 21 melts and fixes the toner image transferred onto the sheet P while conveying the sheet P. After fixing processing is performed by the fixing unit 21, an ejection roller 22 ejects the sheet P.

In FIG. 1, the ultrasonic wave sensor 30 is provided between the pair of secondary transfer rollers 19 and the portion at which the conveyance path from the feed cassette 2 and the conveyance path from the feed tray 3 converge. The purpose of this is to make it possible to determine the type using one ultrasonic wave sensor 30 regardless of whether the sheet P is fed from the feed cassette 2 or the feed tray 3.

Hardware contributing to the operation of the ultrasonic wave sensor 30 and the functions of that hardware will be described next with reference to FIG. 2. The ultrasonic wave transmission unit 31 transmits ultrasonic waves to the sheet P due to a transmission vibration member vibrating in response to a supplied drive signal. The ultrasonic wave reception unit 32 generates a reception signal due to a reception vibration member vibrating due to the ultrasonic waves that were transmitted from the ultrasonic wave transmission unit 31 and have passed through the sheet P. The ultrasonic waves are attenuated when they pass through the sheet P. In the present embodiment, the ultrasonic wave transmission unit 31 transmits ultrasonic waves having a frequency characteristic of 40 kHz, and it is set such that the ultrasonic waves are received by the ultrasonic wave reception unit 32. The frequency of the ultrasonic waves is set in advance. For example, the appropriate range of frequencies is selected according to the configuration, detection accuracy, and the like of the ultrasonic wave transmission unit 31 and the ultrasonic wave reception unit 32. A transmission control unit 33 has a drive signal generation unit 331 that generates a drive signal for transmitting ultrasonic waves, and an amplifier 332 that amplifies the drive signal and supplies it to the ultrasonic wave transmission unit 31. A reception control unit 34 has a detection circuit 342 that detects the ultrasonic waves received by the ultrasonic wave reception unit 32 as voltages, an AD conversion unit 343 that performs analog-digital conversion on the detection signal, a peak extraction unit 344 that extracts the peaks of the ultrasonic waves, and a storage unit 346 that stores the values of the peaks. The control unit 10 reads out the peak values (determination results) from the storage unit 346 and uses them to control image formation conditions such as the conveyance speed and fixing temperature in the fixing unit.

Next, a series of operations will be described. The control unit 10 inputs a measurement start signal indicating the start of measurement to the drive signal control unit 341. Upon receiving the measurement start signal, the drive signal control unit 341 instructs the generation of the drive signal to the drive signal generation unit 331 in order to transmit ultrasonic waves at a predetermined frequency (e.g., 40 kHz). The drive signal is a pulse wave with a constant period. This is determined with consideration given to the fact that the influence of disturbances such as reflection waves caused by the sheet P and members arranged in the periphery of the conveyance path are to be reduced, and the ultrasonic wave reception unit 32 is to be able to receive mainly direct waves emitted by the ultrasonic wave transmission unit 31. This is because the generation of reflection waves and the amplitude of the composite wave composed of the reflection waves generally depend on the wavelength of the ultrasonic waves. There are also cases where a pulse wave with a constant period is referred to as a burst wave. In the present embodiment, five pulses of a 40-kHz pulse wave are input to the ultrasonic wave transmission unit 31 within a 20-ms period. In this way, the drive signal generation unit 331 generates and outputs a signal having a pre-set frequency. The amplifier 332 amplifies the level (voltage value) of the drive signal output by the drive signal generation unit 331 and supplies it to the ultrasonic wave transmission unit 31.

The ultrasonic wave reception unit 32 receives the ultrasonic waves transmitted from the ultrasonic wave transmission unit 31 and outputs a detection signal to the detection circuit 342 of the reception control unit 34. The detection circuit 342 has a function of amplifying the detection signal and a function of rectifying the detection signal. With the amplifying function, the amplification rate can vary between a state in which the sheet P is present between the ultrasonic wave transmission unit 31 and the ultrasonic wave reception unit 32, and a state in which it does not, but the present invention is not limited to this. For example, it is possible to use the same amplification rate in the state in which the sheet P is not present and in the state in which it is present. Also, the rectifying function performs half-wave rectification, but the invention is not limited to this, and it is possible to perform full-wave rectification. An A-D conversion unit 343 converts an analog detection signal generated by the detection circuit 342 into a digital detection signal. The A-D conversion unit 343 performs conversion into a 12-bit digital signal corresponding to the output of the detection circuit 342, but the invention is not limited to this, and it is possible to perform conversion into an appropriate multi-bit digital signal. The peak extraction unit 344 extracts the peaks (local maximums) of the digital signal output from the A-D conversion unit 343. The peak extraction unit 344 stores the peak values extracted at the end of one instance of ultrasonic wave measurement in the storage unit 346. Based on the peak values stored in the storage unit 346, the control unit 10 determines the grammage of the sheet P and controls the operation of the image forming apparatus 1 according to the determination result. The grammage mentioned here is the mass per unit area of a sheet, and the mass per square meter is represented as ($g/m^2$). A clear correlation relationship exists between the peak values and the grammage (or thickness). Accordingly, the control unit 10 can use an equation or a table to determine the grammage (or thickness) based on the peak values.

Figure 3A:
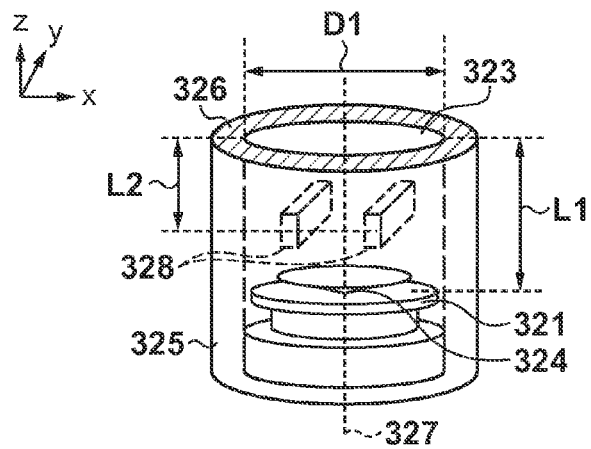
FIGS. 3A to 3C are diagrams showing a configuration of an ultrasonic wave reception unit.
Figure 3B:
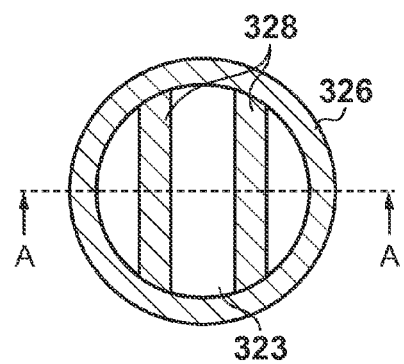
Figure 3C:
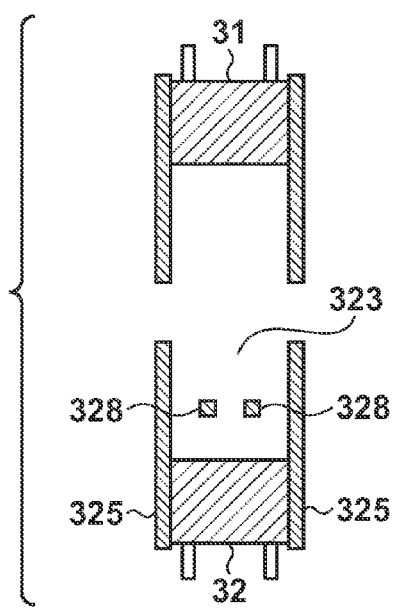

The configuration of the ultrasonic wave reception unit 32 of the ultrasonic wave sensor 30 will be described with reference to FIGS. 3A to 3C. FIG. 3A is a perspective view of the ultrasonic wave reception unit 32, FIG. 3B is a plan view of the ultrasonic wave reception unit 32, and FIG. 3C is a cross-sectional view taken along line A-A of the ultrasonic wave transmission unit 31 and the ultrasonic wave reception unit 32.

In general, the image forming apparatus 1 includes a door 90 that opens and closes in order for the user to manually remove a sheet P if it gets jammed in the internal conveyance path. As described above, the ultrasonic wave transmission unit 31 and the ultrasonic wave reception unit 32 are arranged facing each other on opposite sides of the conveyance path. For this reason, the ultrasonic wave transmission unit 31 and the ultrasonic wave reception unit 32 can be arranged at a position at which it is possible for the user to manually touch them when the door 90 is opened. If the user touches at least one of the ultrasonic wave transmission unit 31 and the ultrasonic wave reception unit 32, it may cause a malfunction and the ultrasonic wave detection accuracy may decrease. In view of this, with the present embodiment, a protection member is provided in the ultrasonic wave reception unit 32 so as to make it difficult for the user to touch the internal member of the ultrasonic wave reception unit 32.

According to FIG. 3A, the ultrasonic wave reception unit 32 has a reception equalizer 324 that amplifies ultrasonic waves, and a reception vibration member 321 that generates a detection signal by vibrating in accordance with ultrasonic waves. A reception guide 325 is provided in the periphery of the ultrasonic wave reception unit 32. As shown in FIG. 3A, the reception guide 325 functions as a tubular guide member that has an opening 323 through which the ultrasonic waves pass and guides the ultrasonic waves. The reception guide 325 extends in the length direction (z-direction) and reduces unnecessary reflection waves. The reception guide 325 in this example is a cylindrical guide, and D1 indicates the opening dimension. As shown in FIG. 3A, L1 indicates the distance from the center of the surface of the reception vibration member 321 to the plane including a reception guide leading end plane 326 (opening plane). Note that the surface of the reception vibration member 321 and the reception guide leading end plane 326 are parallel with the xy plane. L1 is a distance in the length direction (z-direction) of the reception guide 325. The distance L1 is defined as the reception guide length. Note that the reception equalizer 324 may be omitted.

Two protection members 328 are provided in the reception guide 325, between the opening plane of the reception guide 325 and the reception vibration member 321. As shown in FIG. 3A, the two protection members 328 are members that are approximate rectangular cuboids and are provided parallel to the xy plane. Note that the shapes of the protection members 328 may be columnar. Thus, the protection members 328 may be columnar members or plate-shaped members provided parallel to the opening plane. The space between the two protection members 328 and the space in the periphery of the two protection members 328 function as holes/openings/apertures through which the ultrasonic waves pass. In FIG. 3A, L2 indicates the distance from the center of the two protection members 328 to the plane including the reception guide leading end plane 326. The distance L2 is referred to as the protection member distance and is used as a parameter indicating the arrangement position of the protection members 328. Here, the plane including the reception guide leading end plane 326, or in other words, the opening portion of the reception guide 325, is defined as a virtual plane. A line 327 that passes through the center of the reception vibration member 321 and is perpendicular to the surface of the reception vibration member 321 is a virtual line that does not actually exist in the reception vibration member 321. The perpendicular line 327 is a reference for unambiguously determining the distance L1 and the distance L2 from the surface of the reception vibration member 321 to the reception guide leading end plane 326. The perpendicular line 327 is parallel with the z-axis direction.

As shown in FIG. 3A and FIG. 3C, it is possible to give the ultrasonic waves a direction characteristic by surrounding the reception vibration member 321 with the reception guide 325. Furthermore, it is possible to reduce the influence of the reflection waves from the peripheral members using the reception guide 325. By arranging the protective members 328 with respect to the reception guide 325, it is possible to suppress user access from the reception guide leading end plane 326 to the reception vibration member 321, as well as the intrusion of debris or the like into the reception guide 325. According to this, the reception vibration member 321 and the reception equalizer 324 can be protected.

As shown in FIG. 3C, the reception guide 325 is arranged such that the inner circumferential face of the reception guide 325 is in contact with the ultrasonic wave reception unit 32. However, as long as it is possible to suppress user access and the intrusion of debris and the like, the structure in which the ultrasonic wave reception unit 32 and the inner circumferential face of the reception guide 325 are in contact is not mandatory. Resin, for example, can be used as the material for the reception guide 325 and the protection members 328, but other materials such as metal may be used as long as an effect similar to that of the present embodiment can be obtained.

The relationship between the position of the protection members 328 and ultrasonic waves that have passed through a sheet P will be described next with reference to FIG. 4. The results indicated in FIG. 4 were obtained using a sheet P with a grammage of 60 $g/m^2$. The horizontal axis in FIG. 4 indicates the arrangement position of the protection members 328. Here, the arrangement position of the protection members 328 at which the distance L2 is half of the distance L1 is referred to as the center. The arrangement position of the protection members 328 is brought closer to the reception guide leading end plane 326 as it shifts in the positive direction from the center, and it is brought closer to the reception vibration member 321 as it shifts in the negative direction. The numbers written on the horizontal axis are in units of millimeters. The vertical axis indicates the transmission coefficient of the ultrasonic waves. The transmission coefficient is the ratio between the output of the reception control unit 34 at the time when no sheet P is present between the ultrasonic wave transmission unit 31 and the ultrasonic wave reception unit 32, and the output of the reception control unit 34 after receiving the ultrasonic waves that have passed through the sheet P. The solid line indicates the transmission coefficient at the time when there are protection members 328. The broken line indicates the transmission coefficient at the time when there are no protection members 328.

Figure 4:
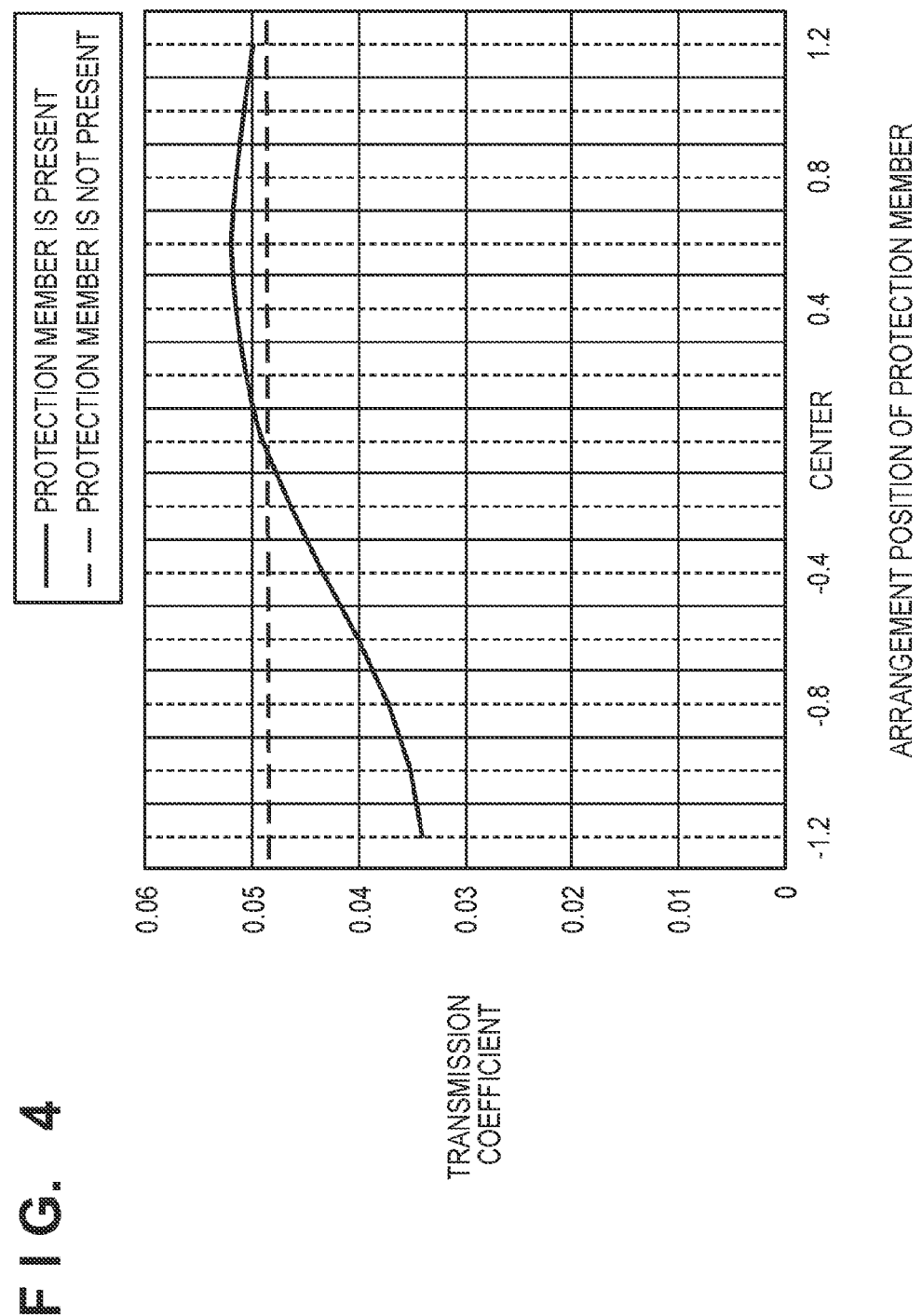
FIG. 4 is a diagram showing a relationship between the arrangement position of a protection member and a transmission coefficient.

According to FIG. 4, it can be understood that the transmission coefficient significantly changes depending on the arrangement position of the protection members 328. Also, the transmission coefficient in the state in which there are no protection members 328 is around 0.049. From FIG. 4, it can be understood that by arranging the protection members 328 in the center (L2=L1/2), a transmission characteristic similar to the transmission characteristic in the case where there are no protection members 328 can be obtained. In other words, by arranging the two protection members 328 in the center, it is possible to reduce the influence of the two protection members 328 on the detection signal for the ultrasonic waves.

Figure 5A:
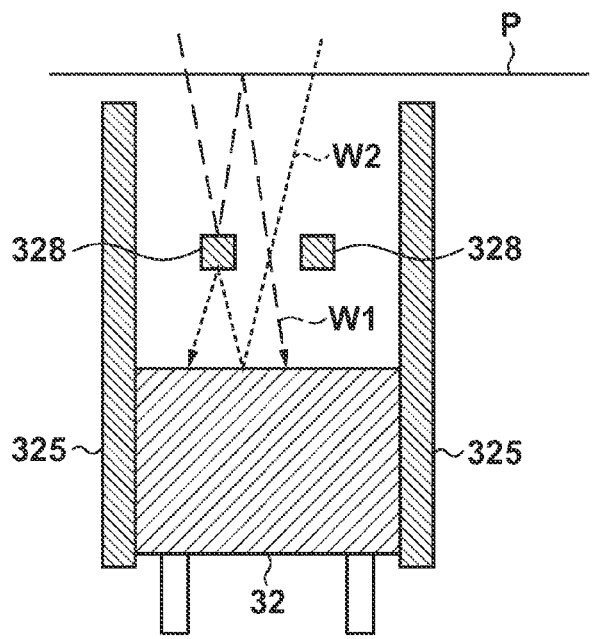
FIGS. 5A to 5C are diagrams showing a composite of multiple reflection waves.
Figure 5B:
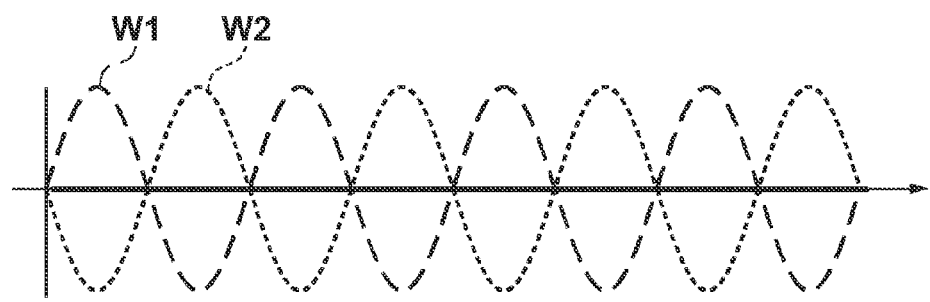

The reason for this will be described next with reference to FIGS. 5A to 5C. Some of the ultrasonic waves output from the ultrasonic wave transmission unit 31 are incident on the ultrasonic wave reception unit 32 after being reflected several times. For example, as shown in FIG. 5A, an ultrasonic wave that has passed through the sheet P is reflected by a protection member 328, is furthermore reflected by the sheet P, and is received by the ultrasonic wave reception unit 32. This is referred to as reflection wave W1. On the other hand, an ultrasonic wave that has passed through the sheet P is reflected by the surface of the ultrasonic wave reception unit 32, is furthermore reflected by the protection member 328, and is received by the ultrasonic wave reception unit 32. This is referred to as reflection wave W2. As shown in FIG. 5B, since the amplitudes of the reflection wave W1 and the reflection wave W2 are approximately the same, if the phases of the reflection wave W1 and the reflection wave W2 differ by 180 degrees, the reflection wave W1 and the reflection wave W2 cancel each other out. This is a state in which the two protection members 328 are arranged such that L2=L1/2. The reason why the phases of W1 and W2 are shifted 180 degrees is because W1 is subjected to fixed-end reflection by the protection member 328 and free-end reflection by the sheet P, whereas W2 is subjected to fixed-end reflection by the vibration member 321 and fixed-end reflection once again by the protection member 328.

Figure 5C:
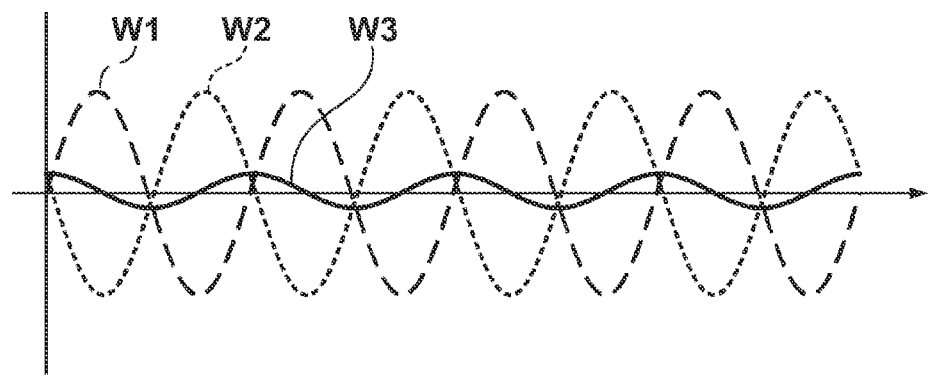

On the other hand, as shown in FIG. 5C, if the phase difference between the reflection wave W1 and the reflection wave W2 is shifted from 180 degrees, a composite wave W3 composed of the reflection wave W1 and the reflection wave W2 appears. For this reason, the transmission coefficient varies in comparison to the time when no protection members 328 are present. Incidentally, FIG. 5C shows waveforms observed at a time when the two protection members 328 are arranged at a position at which L2=L1/2+λ/64. λ is the wavelength of the ultrasonic waves. Thus, by using a position close to the center as the arrangement position of the two protection members 328, the amplitude of the composite wave formed from multiple reflection waves can be made extremely small.

Thus, in the present embodiment, the distance L2 in the length direction of the reception guide 325 from the opening plane of the reception guide 325 to the center of the protection members 328 is half of the length (may be called as distance) L1 in the length direction of the reception guide 325 from the opening plane of the reception guide 325 to the surface of the reception vibration member 321. That is to say, by setting the arrangement position of the protection members 328 to the center (L2=L1/2), a transmission coefficient is obtained that is equal to the transmission coefficient in the case where no protection members 328 are present. In other words, it is possible to protect the reception vibration member 321 without changing the detection characteristic of the ultrasonic wave sensor 30. This relation can be rephrased. On a line that passes through the center of the reception vibration member 321 as the second vibration member and is perpendicular to the surface of the reception vibration member 321, the length from the plane of the reception guide 325 as the second guide member to a surface of the protection members 328 as the second protection member on the leading end plane side of the reception guide 325 is equal to the length from the surface of the reception vibration member 321 to a surface of the protection members 328 on the second vibration member side.

In this way, the position of the protection members 328 has an effect on the accuracy of detecting the ultrasonic waves (and by extension, on the grammage determination accuracy), but the detection accuracy required for the ultrasonic wave sensor 30 depends on the application mode of the ultrasonic wave sensor 30. For example, it is understood from the graph in FIG. 4 that in order to set the accuracy of detecting the sheet P to be within 1% (error), the protection members 328 need to be arranged within a range of being ±0.15 mm from the center. Since the frequency f of the ultrasonic waves is 40 kHz, the wavelength λ is approximately 8.6 mm. The ratio with respect to the wavelength λ at 0.15 mm is 0.15÷8.6≈0.0174. This is approximately 1/57.2. Accordingly, a detection that is accurate to within 1% can be realized within approximately 1/57.2 of the wavelength λ that was calculated using the frequency f of the ultrasonic waves. The detection that is accurate to within 1% is merely an example and it may be based on experience. Thus, the distance L2 may be shifted from the halfway point of the distance L1, within a range in which the required detection accuracy for the ultrasonic waves is satisfied. That is to say, "half" need not be perfectly half, and it is sufficient that it is approximately half. Also, the shift amount of the center of the protection members 328 from the halfway point of the distance L1 need only be a shift amount within a range of ±1/64 the wavelength of the ultrasonic waves, for example. Thus, a length that is roughly half falls within a range of L1/2±1/64 the wavelength of the ultrasonic waves transmitted from the first vibration member.

In the present embodiment, the configuration of the protection members 328 shown in FIGS. 3A to 3C was described as an example. In FIGS. 3A to 3C, the protection members 328 are arranged at a position away from the line connecting the center of the surface of the reception vibration member 321 and the center of the surface of the transmission vibration member. The purpose of this is to guide more direct waves from among the ultrasonic waves to the ultrasonic wave reception unit 32.

Figure 6A:
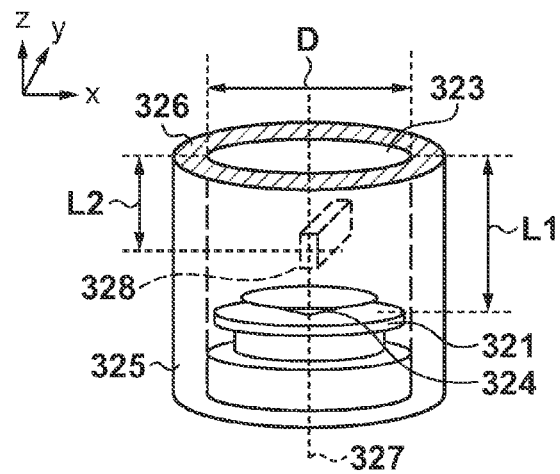
FIGS. 6A to 6C are diagrams showing a configuration of an ultrasonic wave reception unit.
Figure 6B:
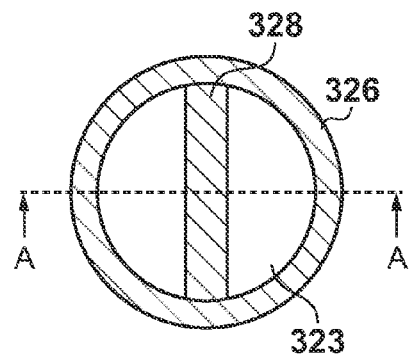
Figure 6C:
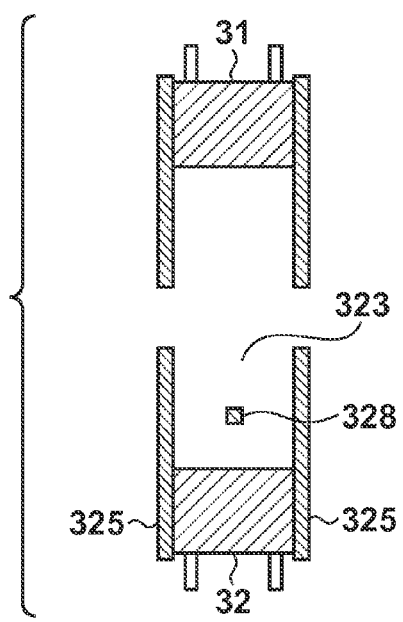

However, as shown in FIGS. 6A to 6C, a configuration may be employed in which one protection member 328 is arranged on the central axis of the reception vibration member 321. Note that FIG. 6A is a perspective view of the ultrasonic wave reception unit 32. FIG. 6B is a plan view.

FIG. 6C is a cross-sectional view taken along line A-A of the ultrasonic wave transmission unit 31 and the ultrasonic wave reception unit 32.

With this kind of configuration as well, the relationship between the arrangement position of the protection member 328 and the transmission coefficient is similar to the characteristic shown in FIG. 4. Accordingly, even if one protection member 328 is arranged in the center, the transmission coefficient in the case where no protection members 328 are present is obtained. Note that there are cases where the dimension in the x direction of the protection member 328 needs to be increased in order to set the strength of the protection member 328 to a target strength. In such a case, there is a possibility that the reception intensity of the ultrasonic waves will decrease. This is because the position at which the intensity of the ultrasonic waves is the greatest is on the central axis of the reception vibration member 321. Accordingly, by arranging the protection member 328 such that nothing is on the central axis of the reception vibration member 321 as shown in FIGS. 3A to 3C, the ultrasonic wave reception unit 32 can receive the ultrasonic waves transmitted from the ultrasonic wave transmission unit 31 with accuracy.

Second Embodiment

The first embodiment described an example in which the protection members 328 are arranged with respect to the ultrasonic wave reception unit 32. The second embodiment will describe an example in which protection members are arranged in both the ultrasonic wave transmission unit 31 and the ultrasonic wave reception unit 32. Note that configurations that are similar to those of the first embodiment such as that of the sheet determination apparatus are omitted so as to simplify the description.

Figure 7A:
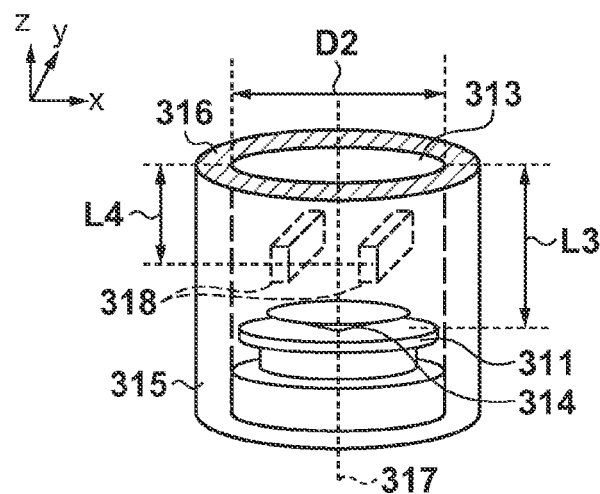
FIGS. 7A to 7C are diagrams showing a configuration of an ultrasonic wave transmission unit.
Figure 7B:
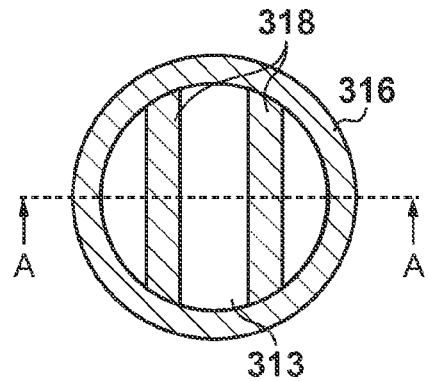
Figure 7C:
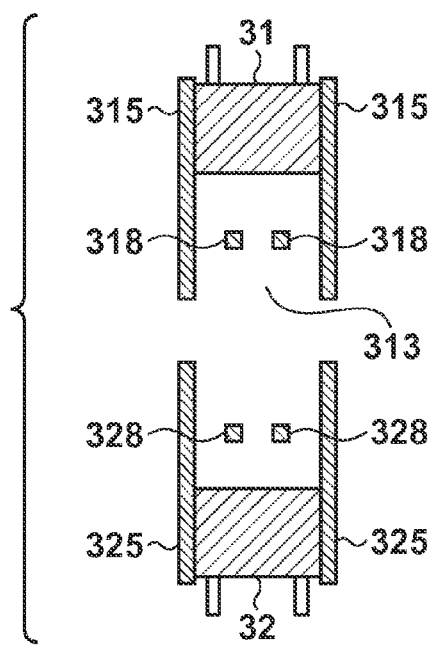

The configurations of the ultrasonic wave transmission unit 31 and the ultrasonic wave reception unit 32 of the ultrasonic wave sensor 30 in the second embodiment are shown in FIGS. 7A to 7C. FIG. 7A is a perspective view of the ultrasonic wave transmission unit 31. FIG. 7B is a plan view of the ultrasonic wave transmission unit 31. FIG. 7C is a cross-sectional view taken along line A-A which shows the positional relationship between the ultrasonic wave transmission unit 31 and the ultrasonic wave reception unit 32. It is assumed that these units are arranged at a position at which the user can touch the ultrasonic wave transmission unit 31 and the ultrasonic wave reception unit 32 when the user opens the door of the main body. Note that the ultrasonic wave transmission unit 31 and the ultrasonic wave reception unit 32 may be arranged at a position at which they are difficult to touch.

The transmission vibration member 311 is a member that transmits ultrasonic waves by vibrating according to a drive signal supplied from the transmission control unit 33. A transmission guide 315 is provided in the periphery of the ultrasonic wave transmission unit 31. As shown in FIG. 7A, the transmission guide 315 functions as a tubular guide member that has an opening 313 through which ultrasonic waves pass and guides the ultrasonic waves. The transmission guide 315 extends in the length direction (z-direction) and reduces unnecessary reflection waves. The transmission guide 315 in this example is a cylindrical guide, and D2 indicates the opening dimension. As shown in FIG. 5A, L3 indicates the distance from the center of the circular surface of the transmission vibration member 311 to a plane including a transmission guide leading end plane 316 (opening plane). Note that the surface of the transmission vibration member 311 and the transmission guide leading end plane 316 are parallel with the xy plane. L3 is the distance in the length direction (z-direction) of the transmission guide 315. The distance L3 is defined as the transmission guide length. A transmission equalizer 314 is a member for amplifying the ultrasonic waves transmitted by the transmission vibration member 311. Note that it is possible to transmit ultrasonic waves using a configuration that does not include the transmission equalizer 314, as long as the transmission vibration member 311 is present.

Two protection members 318 are provided in the transmission guide 315, between the opening plane of the transmission guide 315 and the transmission vibration member 311. As shown in FIG. 7A, the two protection members 318 are members that are approximate rectangular cuboids and are provided parallel with the xy plane. Note that the shapes of the protection members 318 may be columnar. Thus, the protection members 318 may be columnar members or plate-shaped members provided parallel to the opening plane. In FIG. 7A, L4 indicates the distance from the center of the two protection members 318 to the plane including the transmission guide leading end plane 316. The distance L4 is referred to as the protection member distance and is used as a parameter indicating the arrangement position of the protection members 318. Here, the plane including the transmission guide leading end plane 316, or in other words, the opening portion of the transmission guide 315, is defined as a virtual plane. A line 317 that passes through the center of the transmission vibration member 311 and is perpendicular to the surface of the transmission vibration member 311 is a virtual line that does not actually exist in the transmission vibration member 311. The perpendicular line 317 is a reference for unambiguously determining the distance L2 and the distance L1 from the surface of the transmission vibration member 311 to the transmission guide leading end plane 316. The perpendicular line 317 is parallel with the z-axis direction.

As shown in FIG. 7A and FIG. 7C, it is possible to restrict the propagation direction of the ultrasonic waves and give the ultrasonic waves a direction characteristic by surrounding the transmission vibration member 311 with the transmission guide 315. By arranging the protection members 318 with respect to the transmission guide 315, it is possible to suppress user access from the transmission guide leading end plane 316 to the transmission vibration member 311, as well as debris and the like intruding in the transmission guide 315. According to this, the transmission vibration member 311 and the transmission equalizer 314 can be protected.

As shown in FIG. 7C, the transmission guide 315 is arranged such that the inner circumferential face of the transmission guide 315 is in contact with the ultrasonic wave transmission unit 31. However, the structure in which the ultrasonic wave transmission unit 31 and the inner circumferential face of the transmission guide 315 are in contact is not mandatory as long as it is possible to suppress user access and the intrusion of debris and the like. For example, it is possible to use resin as the material for the transmission guide 315 and the protection members 318, but other materials such as metal may be used as long as an effect similar to that of the present embodiment can be obtained.

The relationship between the position of the protection members 318 and 328 and ultrasonic waves that have passed through a sheet P will be described next with reference to FIG. 8. The results indicated in FIG. 8 were obtained using a sheet P with a grammage of 60 g/m$^2$. The horizontal axis in FIG. 8 indicates the arrangement position of the protection members 318 and 328. Here, the position at which the protection members 328 are arranged such that the distance L2 is half of the distance L1 and the protection members 318 are arranged such that the distance L4 is half of the distance L3 is referred to as the center. The arrangement position of the protection member 328 is brought closer to the reception guide leading end plane 326 as it shifts in the positive direction from the center, and it is brought closer to the reception vibration member 321 as it shifts in the negative direction. Also, the arrangement position of the protection member 318 is brought closer to the transmission guide leading end plane 316 as it shifts in the positive direction from the center, and it is brought closer to the transmission vibration member 311 as it shifts in the negative direction. The protection members 318 and 328 are moved by the same amount. The numbers written on the horizontal axis are in units of millimeters. The vertical axis indicates the transmission coefficient of the ultrasonic waves. The transmission coefficient is the ratio between the output of the reception control unit 34 at the time when no sheet P is present between the ultrasonic wave transmission unit 31 and the ultrasonic wave reception unit 32, and the output of the reception control unit 34 after receiving the ultrasonic waves that have passed through the sheet P. The solid line indicates the transmission coefficient at the time when the protection members 318 and 328 are present. The broken line indicates the transmission coefficient at the time when the protection members 318 and 328 are not present.

Figure 8:
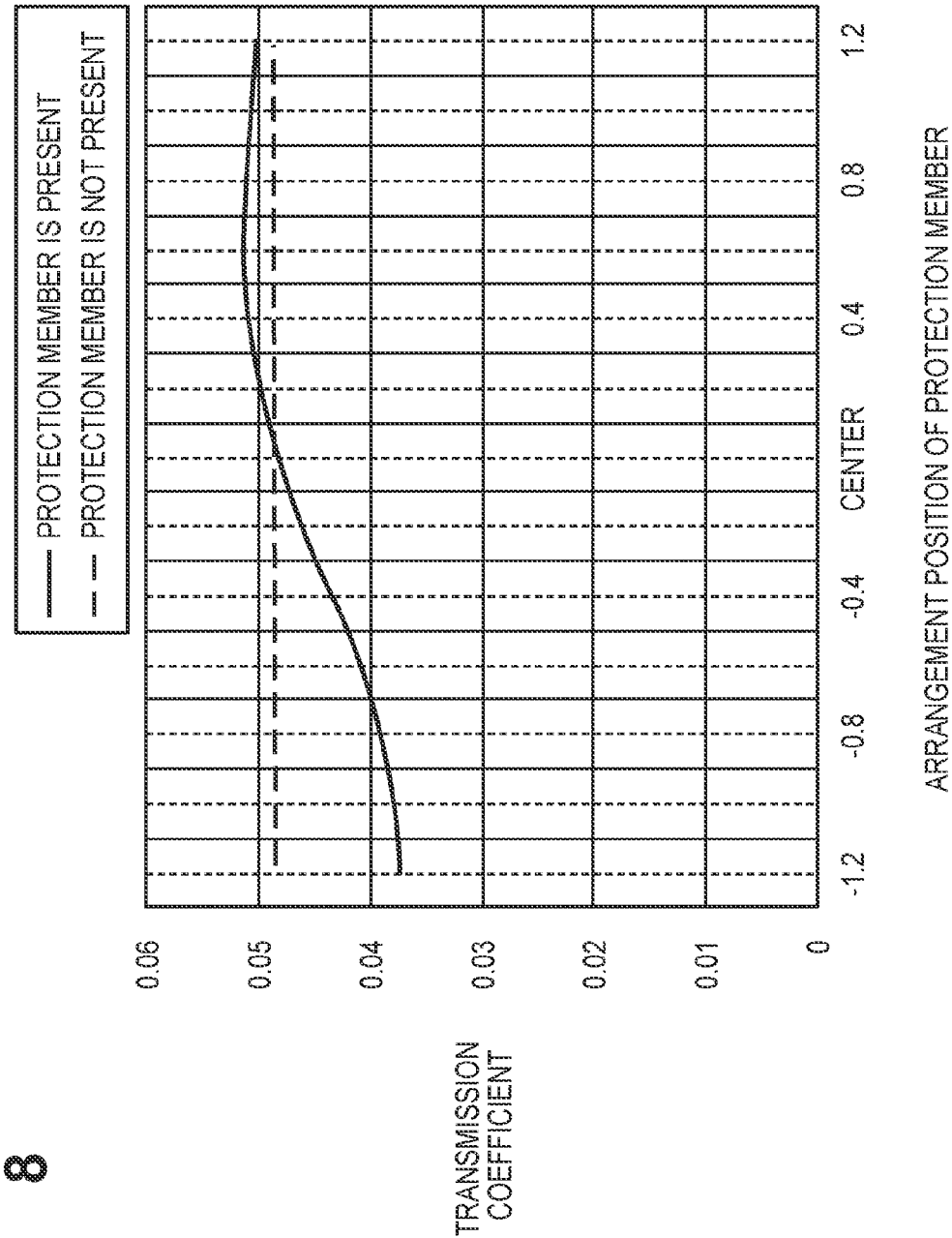
FIG. 8 is a diagram showing a relationship between the arrangement position of a protection member and a transmission coefficient.

According to FIG. 8, it can be understood that the transmission coefficient significantly changes depending on the arrangement positions of the protection members 318 and 328. Also, the transmission coefficient in the state in which the protection members 318 and 328 are not present is around 0.049. From FIG. 8, it can be understood that by arranging the protection members 318 and 328 in the center (L4=L3/2, L2=L1/2), a transmission characteristic can be obtained that is similar to the transmission characteristic in the case where the protection members 318 and 328 are present. In other words, by arranging the two protection members 318 and 328 in the center, it is possible to reduce the influence that the two protection members 318 and 328 have on the ultrasonic wave detection signal. This relation between L3 and L4 can be also rephrased. On a line that passes through the center of the transmission vibration member 311 as the first vibration member and is perpendicular to the surface of the transmission vibration member 311, the length from the plane of the transmission guide 315 as the first guide member to a surface of the protection members 318 as the first protection member on the leading end plane side of the transmission guide 315 is equal to the length from the surface of the transmission vibration member 311 to a surface of the protection members 318 on the transmission vibration member 311.

In this way, the distance (L2, L4) in the length direction of the guide member from the opening plane of the guide member to the center of the protection member is half of the distance (L1, L3) in the length direction of the guide member from the opening plane of the guide member to the surface of the whichever of the transmission vibration member and the reception vibration member is provided in the guide member, or the distance is shifted from the halfway point within a range in which the required accuracy for detecting the ultrasonic waves is satisfied. For example, regarding the ultrasonic wave transmission unit 31, the distance L4 in the length direction of the transmission guide 315 from the opening plane of the transmission guide 315 to the center of the protection member 318 is half of the distance L3 in the length direction of the transmission guide 315 from the opening plane of the transmission guide 315 to the surface of the transmission vibration member 311. In other words, the arrangement position of the two protection members 318 is set to the center (L4=L3/2), and thereby a transmission coefficient is obtained that is equal to the transmission coefficient in the case where no protection members 318 are present. In other words, it is possible to protect the transmission vibration member 311 without changing the detection characteristic of the ultrasonic wave sensor 30. As described in the first embodiment, the distance L4 may be shifted from the halfway point of the distance L3, within a range in which the required accuracy for detecting the ultrasonic waves is satisfied. Also, the shift amount of the center of the protection members 318 from the halfway point of the distance L3 need only be a shift amount within a range of ±1/64 of the wavelength of the ultrasonic waves, for example.

Also, in comparison to FIG. 4, in FIG. 8, it can be understood that the ratio of the change in the transmission coefficient depending on the arrangement position is smaller. For this reason, by arranging the protection member 318 and the protection member 328 such that they are in the same relationship with respect to the vibration member and the opening plane, it is possible to reduce the precision required for the arrangement positions of the protection members.

Also, in the second embodiment, two protection members are provided on the transmission side and on the reception side. In particular, in FIGS. 7A to 7C, the protection members 328 and 318 are arranged at a position away from the line connecting the center of the surface of the reception vibration member 321 and the center of the surface of the transmission vibration member 311. This is because more direct waves from among the ultrasonic waves are guided to the ultrasonic wave reception unit 32. Note that one protection member may be arranged on both the transmission side and the reception side, and it is possible for two protection members to be arranged on one side and one protection member to be arranged on the other side. Note that in FIGS. 6A to 6C, one protection member is arranged on the line connecting the center of the surface of the reception vibration member 321 and the center of the surface of the transmission vibration member 311, but the one protection member may be arranged at a position away from the line.

Third Embodiment

The first embodiment described a configuration in which the protection members 328 are arranged with respect to the ultrasonic wave reception unit 32. The second embodiment described a configuration in which protection members are arranged not only at the ultrasonic wave reception unit 32, but also at the ultrasonic wave transmission unit 31. The third embodiment will describe a configuration in which the protection member 318 is arranged only at the ultrasonic wave transmission unit 31. Note that the description of configurations similar to those of the first embodiment and the second embodiment will not be repeated.

Figure 9A:
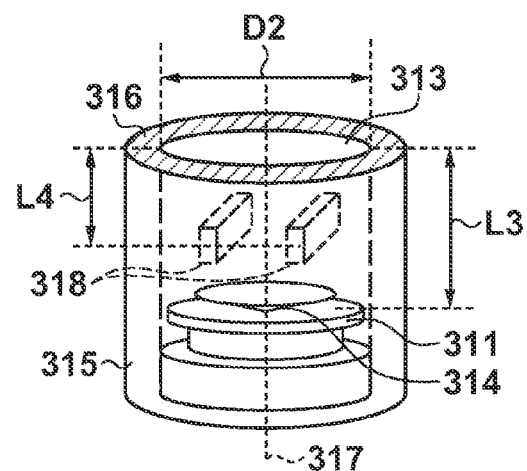
FIGS. 9A to 9C are diagrams showing a configuration of an ultrasonic wave transmission unit.
Figure 9B:
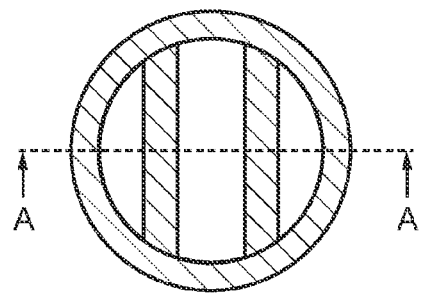
Figure 9C:
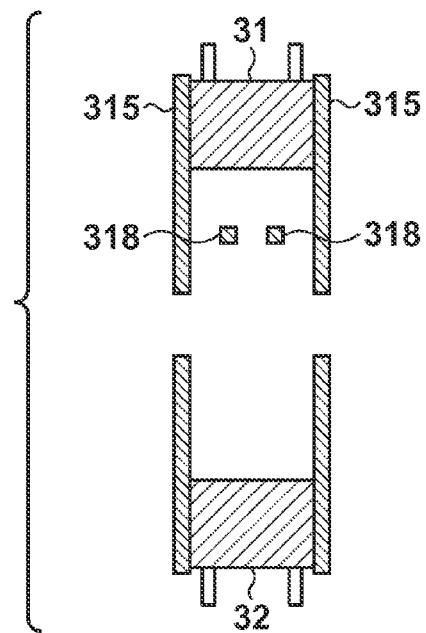

The configuration of the ultrasonic wave transmission unit 31 of the ultrasonic wave sensor 30 will be described below with reference to FIGS. 9A to 9C. FIG. 9A is a perspective view of the ultrasonic wave transmission unit 31. FIG. 9B is a plan view of the ultrasonic wave transmission unit 31. FIG. 9C is a cross-sectional view taken along line A-A which shows the positional relationship between the ultrasonic wave transmission unit 31 and the ultrasonic wave reception unit 32. By comparing FIGS. 9A, 9B, 7A, and 7B, it can be understood that the configuration of the ultrasonic wave transmission unit 31 is as described above. Note that upon comparing FIGS. 9C and 7C, it can be understood that no protection member 328 is attached to the ultrasonic wave reception unit 32. Thus, in the third embodiment the protection member 318 is arranged only at the ultrasonic wave transmission unit 31.

The relationship between the arrangement position of the protection member 318 and the transmission coefficient in the third embodiment will be described next with reference to FIG. 10. The grammage of the sheet P is 60 g/m². The horizontal axis in FIG. 10 indicates the arrangement position of the protection members 318. Here, the arrangement position of the protection members 318 at which the distance L4 is half of the distance L3 is referred to as the center. The arrangement position of the protection members 318 is brought closer to the transmission guide leading end plane 316 as it shifts in the positive direction from the center, and it is brought closer to the transmission vibration member 311 as it shifts in the negative direction. The numbers written on the horizontal axis are in units of millimeters. The vertical axis indicates the transmission coefficient of the ultrasonic waves.

According to FIG. 10, it can be understood that the transmission coefficient changes depending on the arrangement position of the protection member 318. Also, the transmission coefficient of the sheet P in the state in which no protection member 318 is present is around 0.049. Accordingly, by arranging the protection member 318 in the center (L4=L3/2), the influence of the protection member 318 can be made extremely small. Note that the arrangement position can be offset within a certain range from the center in accordance with the required detection accuracy. This matter has been described above.

By arranging the protection member 318 at the center, the influence that the protection member 318 has on the reception intensity of the ultrasonic waves can be reduced and the ultrasonic wave vibration members can be protected from foreign objects. Note that in the third embodiment, two protection members 318 were employed, but one protection member may be employed as described with reference to FIGS. 6A to 6C.

Other Remarks

The first embodiment to the third embodiment described examples of employing one or two rectangular cuboid protection members. However, a different number may be provided and the protection members may have different shapes. FIGS. 11A to 11D are plan views showing examples of guides and protection members. As illustrated in the first embodiment to third embodiment, the thickness in the z direction of the protection members may be a constant width.

Figure 11A:
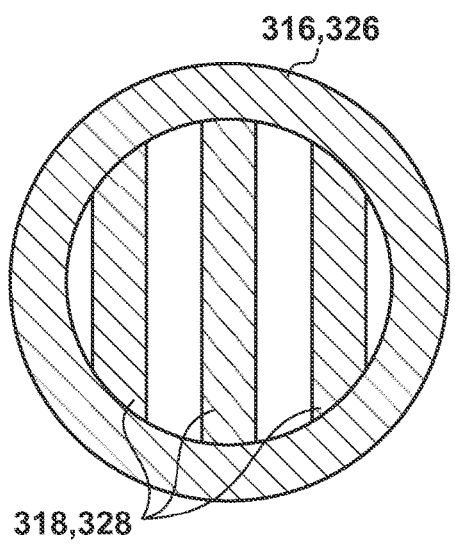
FIGS. 11A to 11D are diagrams showing other examples of protection members.
Figure 11B:
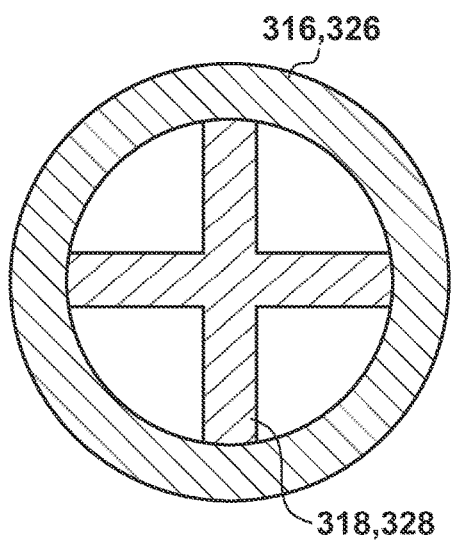
Figure 11C:
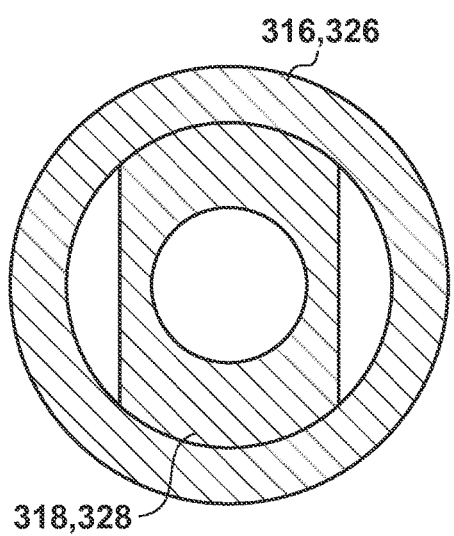
Figure 11D:
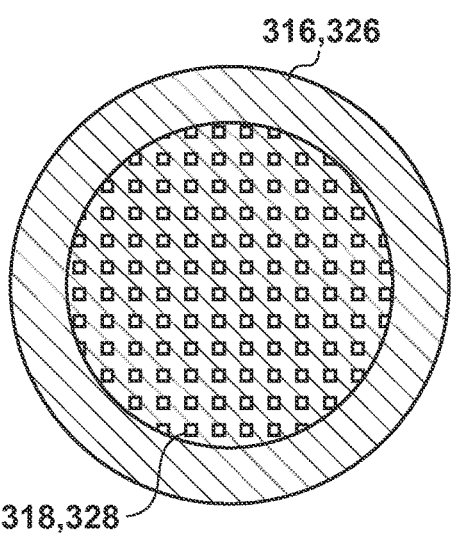

As shown in FIG. 11A, there may be three or more protection members 318 and 328. As shown in FIG. 11B, cross-shaped protection members 318 and 328 may be employed. As shown in FIG. 11C, protection members 318 and 328 that are obtained by providing a circular or rectangular hole in the center of a plate-shaped main member may be employed. As shown in FIG. 11D, net-shaped or grid-shaped protection members 318 and 328 may be employed. Note that regardless of the shape, the arrangement position of the protection members 318 and 328 are positions corresponding to half of the distances L1 and L3 from the opening plane of the guide to the vibration member, or are positions that have been shifted somewhat in the z-direction from the halfway point. Thus, the influence that the protection members 318 and 328 have on the reception intensity of the ultrasonic waves can be reduced and the ultrasonic wave vibration members can be protected from foreign objects.

In the second embodiment, the shape and number of the protection members 318 and 328 match. The guide and the protection members can be used in common in the ultrasonic wave transmission unit 31 and the ultrasonic wave reception unit 32, which is effective for reducing cost. Also, since the ultrasonic wave transmission unit 31 and the ultrasonic wave reception unit 32 can also have the same parts, if the shape and number of the protection members 318 and 328 match, it is effective for reducing cost. Note that it is not mandatory that the shape and number of the protection members 318 and 328 match, and the shape and number of the protection members 318 and 328 may be different. Note that the arrangement position of the protection members 318 and 328 are positions corresponding to half of the distances L1 and L3 from the opening plane of the guide to the vibration member.

It was mentioned that the protection members are provided on only one of the ultrasonic wave transmission unit 31 and the ultrasonic wave reception unit 32. In such a case, the one of the ultrasonic wave transmission unit 31 and the ultrasonic wave reception unit 32 that is not provided with a protection member may be arranged at a position at which it is difficult for the user to touch with his or her fingers. Also, the ultrasonic wave transmission unit 31 may be rotated using a motor so as to be moved to a position at which the user cannot touch it with his or her fingers.

By employing the aforementioned ultrasonic wave sensor in a sheet determination apparatus that determines the type of a sheet, the ultrasonic wave sensor can be protected and the accuracy of determining the type of sheet can be maintained. Also, this kind of sheet determination apparatus may be applied to the image forming apparatus 1. In such a case, the control unit 10 functions as a control unit that controls the image formation condition used by the image forming unit according to the determination result of the sheet determination apparatus. According to this, it is possible to set the appropriate image formation condition (sheet conveyance speed or fixing temperature in the fixing unit 21) according to the type (grammage or thickness) of the sheet. As a result, toner images without irregularities can be formed on sheets having different types as well.

The ultrasonic wave sensor in the present embodiment may be employed in an image scanning apparatus. There are cases where an automatic document feeding apparatus of an image scanning apparatus employs an ultrasonic wave sensor in order to detect the feeding of overlapping sheets. By suppressing the intrusion of foreign objects in this kind of ultrasonic wave sensor as well, the detection accuracy of the ultrasonic wave sensor can be maintained and malfunction can be suppressed.

Figure 12A:
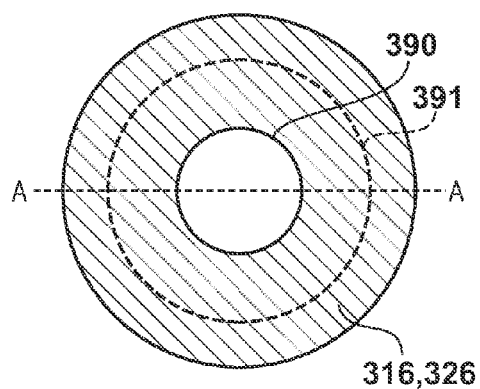
FIGS. 12A and 12B are plain views of the ultrasonic wave transmission unit 31 and the ultrasonic wave reception unit 32.
Figure 12B:
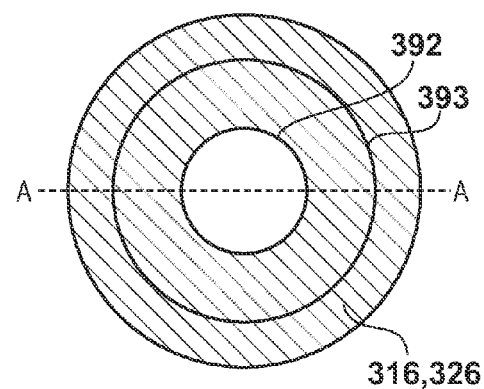
Figure 12C:
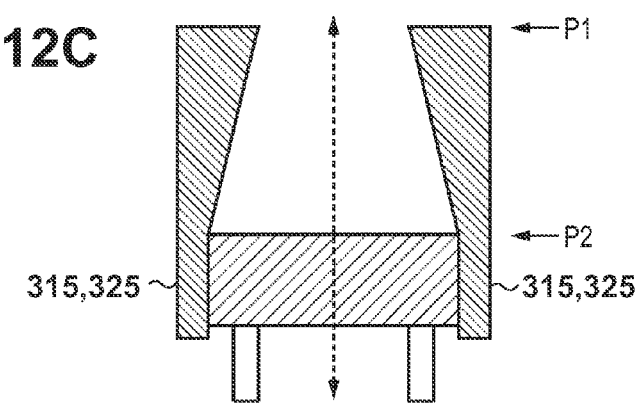
FIG. 12C is an A-A sectional view corresponding to the plain view of FIG. 12A.
Figure 12D:
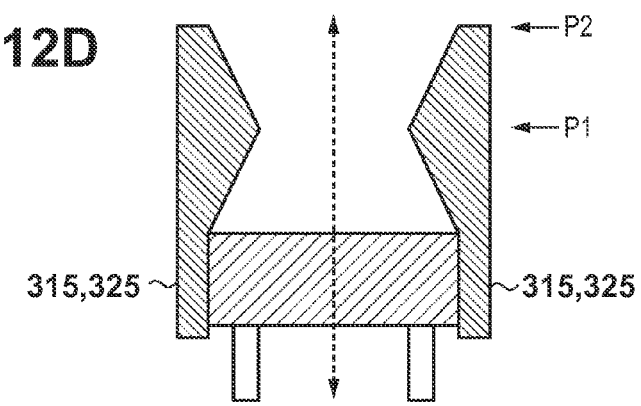
FIG. 12D is an A-A sectional view corresponding to the plain view of FIG. 12B.

The present embodiment described a cylindrical guide member whose cross-sectional area is constant in the xy-direction, but it is possible to use a cylindrical guide member whose cross-sectional area in the xy direction gradually changes. For example, the cross-sectional area in the xy-direction may increase or decrease from the vibration member side to the opening side. A guide member with this kind of tapering (e.g. horn shape, reversed horn shape or sandglass like shape having constricted part) may be employed. The cross-sectional shape may be circular, elliptical, rectangular, or the like. That is, in a direction on a line that passes through the center of the vibration member and is perpendicular to a surface on a side of the vibration member that receives or transmits ultrasonic waves, an aperture size (cross-sectional area) of the guide member at a first position where the protection portion is provided with the guide member is smaller than an aperture size of the guide member at a second position where the protection portion is not provided with the guide member. In other words, an inner diameter of the guide member at the first position is smaller than that of the guide member at the second position. FIGS. 12A-12D show examples of these arrangements. FIGS. 12A and 12B are plain views of the ultrasonic wave transmission unit 31 and the ultrasonic wave reception unit 32. FIG. 12C is A-A sectional view corresponding to the plain view of FIG. 12A. FIG. 12D is A-A sectional view corresponding to the plain view of FIG. 12B. In FIG. 12A, an aperture 390 is an aperture corresponding to a first position P1 shown in FIG. 12C. An aperture 391 is an aperture corresponding to a second position P2 shown in FIG. 12C. In FIG. 12C, shapes of the transmission guide 315 and the reception guide 325 are reversed horn shapes. In FIG. 12B, an aperture 392 is an aperture corresponding to a first position P1 shown in FIG. 12D. An aperture 393 is an aperture corresponding to a second position P2 shown in FIG. 12D. In FIG. 12D, shapes of the transmission guide 315 and the reception guide 325 are sandglass like shapes. A constricted part of the guide member works as a protection member or a protection portion. That is, the guide member and the protection member may be integrated or unified. The constricted part of the guide member makes it difficult for a user to touch the vibrating member. The aperture shape may be circle or more complicated shape.

In a direction on a line that passes through the center of the vibration member and is perpendicular to a surface on a side of the vibration member that transmits or receives ultrasonic waves, a part of the vibration member may overlap the protection member.

The image formation condition may be a conveyance speed of the sheet or a fixing temperature for fixing a toner image onto the sheet or a voltage value for transferring a toner image onto the sheet.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2013-162796, filed Aug. 5, 2013, and 2014-133248, filed Jun. 27, 2014, and 2014-155778 filed Jul. 31, 2014 which are hereby incorporated by reference herein in their entirety.

What is claimed is:

1. An ultrasonic wave transmission unit comprising:
   a vibration member that vibrates so as to transmit ultrasonic waves;
   a guide member that guides ultrasonic waves transmitted from the vibration member; and
   a protection member that protects the vibration member and that is provided in the guide member,
   wherein in viewing from an exit of the ultrasonic waves to the vibration member along with a direction on a line that passes through a center of the vibration member and is perpendicular to a surface on a side of the vibration member that transmits the ultrasonic waves, an area corresponding to the vibration member is divided into a plurality of areas by the protection member, and
   wherein the ultrasonic wave transmission unit is exposed when a door of an apparatus which is provided with the ultrasonic wave transmission unit is opened.

2. The ultrasonic wave transmission unit according to claim 1, wherein
   one or more members are provided as the protection member.

3. The ultrasonic wave transmission unit according to claim 1, wherein
   the protection member is arranged at a position away from the line that passes through the center of the vibration member and is perpendicular to the surface of the vibration member.

4. An ultrasonic wave transmission unit comprising:
   a vibration member that vibrates so as to transmit ultrasonic waves;
   a guide member that guides ultrasonic waves transmitted from the vibration member; and
   a protection member that protects the vibration member and that is provided in the guide member,
   wherein in viewing from an exit of the ultrasonic waves to the vibration member along with a direction on a line that passes through a center of the vibration member and is perpendicular to a surface on a side of the vibration member that transmits the ultrasonic waves, a part of the vibration member overlaps the protection member, and
   on the line, a distance from a virtual plane including a leading end plane of the guide member to the center of the protection member is approximately half of a distance from the virtual plane to the surface.

5. The ultrasonic wave transmission unit according to claim 4, wherein
   the protection member is provided parallel to the virtual plane.

6. The ultrasonic wave transmission unit according to claim 5, wherein
   on the line, a distance from the virtual plane to a surface of the protection member on a side that faces the leading end plane of the guide member is equal to a distance from the surface of the vibration member to a surface of the protection member on a side that faces the vibration member.

7. The ultrasonic wave transmission unit according to claim 4, wherein
   the approximately half is in a range of ±1/64 the wavelength of ultrasonic waves transmitted from the vibration member as a reference to half of the distance from the virtual plane to the surface.

8. A sheet determination apparatus for determining a type of a sheet, the sheet determination apparatus comprising:
   an ultrasonic wave sensor that includes:
   a transmission unit including a vibration member that vibrates so as to transmit ultrasonic waves and a guide member that guides ultrasonic waves transmitted from the vibration member to the sheet, and a protection member that protects the vibration member and that is provided in the guide member; and
   a reception unit that receives ultrasonic waves that have been transmitted from the vibration member and attenuated via the sheet, and
   a determination unit that determines the type of the sheet based on the ultrasonic waves received by the reception unit,
   wherein in viewing from an exit of the ultrasonic waves to the vibration member along with a direction on a line that passes through a center of the vibration member and is perpendicular to a surface of the vibration member on a side that transmits the ultrasonic waves, an area corresponding to the vibration member is divided into a plurality of areas by the protection member, and wherein the sheet determination apparatus is exposed when a door of an apparatus which is provided with the sheet determination apparatus is opened.

9. The sheet determination apparatus according to claim 8, wherein the type of the sheet is the grammage or thickness of the sheet.

10. An image forming apparatus comprising:

an ultrasonic wave sensor that includes:

a transmission unit including a first vibration member that vibrates so as to transmit ultrasonic waves and a first guide member that guides ultrasonic waves transmitted from the first vibration member to a sheet, and a first protection member that protects the first vibration member and that is provided in the first guide member; and a reception unit that receives ultrasonic waves that have been transmitted from the first vibration member and attenuated via the sheet, an image forming unit that forms an image on the sheet; and a control unit that controls an image formation condition used by the image forming unit according to ultrasonic waves received by the reception unit, wherein in viewing from an exit of the ultrasonic waves to the vibration member along with a direction on a line that passes through a center of the first vibration member and is perpendicular to a surface of the first vibration member on a side that transmits the ultrasonic waves, an area corresponding to the vibration member is divided into a plurality of areas by the protection member, wherein the transmission unit and the reception unit are arranged to face each other via a conveyance path of the sheet, and wherein the transmission unit is exposed when a door is opened to remove a sheet jammed on the conveyance path.

11. The image forming apparatus according to claim 10, wherein the image formation condition is a conveyance speed of the sheet or a fixing temperature for fixing a toner image onto the sheet or a voltage value for transferring a toner image onto the sheet.

12. The image forming apparatus according to claim 10, wherein the reception unit includes:

a second vibration member that vibrates by receiving ultrasonic waves that have been transmitted from the first vibration member and attenuated via the sheet;

a second guide member that guides ultrasonic waves attenuated via the sheet to the second vibration member; and a second protection member that protects the second vibration member and that is provided in the second guide member wherein in viewing from an entrance of the ultrasonic waves to the second vibration member along with a direction on a line that passes through a center of the second vibration member and is perpendicular to a surface of the second vibration member on a side that receives the ultrasonic waves, an area corresponding to the second vibration member is divided into a plurality of areas by the second protection member.

13. The image forming apparatus according to claim 12, wherein the transmission unit and the reception unit are arranged to face each other via a conveyance path of the sheet, and wherein at least one of the transmission unit and the reception unit is exposed when the door is opened to remove a sheet jammed on the conveyance path.

14. An ultrasonic wave reception unit comprising:

a vibration member that vibrates by receiving ultrasonic waves;

a guide member that guides ultrasonic waves to the vibration member; and a protection member that protects the vibration member and that is provided in the guide member, wherein in viewing from an entrance of the ultrasonic waves to the vibration member along with a direction on a line that passes through a center of the vibration member and is perpendicular to a surface on a side of the vibration member that receives the ultrasonic waves, an area corresponding to the vibration member is divided into a plurality of areas by the protection member, and wherein the ultrasonic wave reception unit is exposed when a door of an apparatus which is provided with the ultrasonic wave reception unit is opened.

15. The ultrasonic wave reception unit according to claim 14, wherein one or more members are provided as the protection member.

16. The ultrasonic wave reception unit according to claim 14, wherein the protection member is arranged at a position away from the line that passes through the center of the vibration member and is perpendicular to the surface of the vibration member.

17. An ultrasonic wave reception unit comprising:

a vibration member that vibrates by receiving ultrasonic waves;

a guide member that guides ultrasonic waves to the vibration member; and a protection member that protects the vibration member and that is provided in the guide member, wherein in viewing from an entrance of the ultrasonic waves to the vibration member along with a direction on a line that passes through a center of the vibration member and is perpendicular to a surface on a side of the vibration member that receives the ultrasonic waves, a part of the vibration member overlaps the protection member, and on the line, a distance from a virtual plane including a leading end plane of the guide member to the center of the protection member is approximately half of a distance from the virtual plane to the surface.

18. The ultrasonic wave reception unit according to claim 17, wherein the protection member is provided parallel to the virtual plane.

19. The ultrasonic wave reception unit according to claim 18, wherein on the line, a distance from the virtual plane to a surface of the protection member on a side that faces the leading end plane of the guide member is equal to a distance from the surface of the vibration member to a surface of the protection member on a side that faces the vibration member.

20. The ultrasonic wave reception unit according to claim 17, wherein
the approximately half is in a range of ±1/64 the wavelength of ultrasonic waves received by the vibration member as a reference to half of the distance from the virtual plane to the surface.

21. A sheet determination apparatus for determining a type of a sheet, the sheet determination apparatus comprising:
an ultrasonic wave sensor that includes:
a transmission unit that transmits ultrasonic waves; and
a reception unit including a vibration member that vibrates by receiving ultrasonic waves that have been transmitted from the transmission unit and attenuated via the sheet and a guide member that guides ultrasonic waves attenuated via the sheet to the vibration member, and a protection member that protects the vibration member and that is provided in the guide member,
a determination unit that determines the type of the sheet based on ultrasonic waves received by the reception unit,
wherein
in viewing from an entrance of the ultrasonic waves to the vibration member along with a direction on a line that passes through a center of the vibration member and is perpendicular to a surface of the vibration member on a side that receives ultrasonic waves, an area corresponding to the vibration member is divided into a plurality of areas by the protection member, and
wherein the sheet determination apparatus is exposed when a door of an apparatus which is provided with the sheet determination apparatus is opened.

22. The sheet determination apparatus according to claim 21, wherein
the type of the sheet is the grammage or thickness of the sheet.

23. An image forming apparatus comprising:
an ultrasonic wave sensor that includes:
a transmission unit that transmits ultrasonic waves; and
a reception unit including a vibration member that vibrates by receiving ultrasonic waves that have been transmitted from the transmission unit and attenuated via a sheet and a guide member that guides ultrasonic waves attenuated via the sheet to the vibration member, and a protection member that protects the vibration member and that is provided in the guide member,
an image forming unit that forms an image on the sheet; and
a control unit that controls an image formation condition used by the image forming unit according to ultrasonic waves received by the reception unit,
wherein
in viewing from an entrance of the ultrasonic waves to the vibration member along with a direction on a line that passes through a center of the vibration member and is perpendicular to a surface of the vibration member on a side that receives ultrasonic waves, an area corresponding to the vibration member is divided into a plurality of areas by the protection member,
wherein the transmission unit and the reception unit are arranged to face each other via a conveyance path of the sheet, and
wherein the reception unit is exposed when a door is opened to remove a sheet jammed on the conveyance path.

24. The image forming apparatus according to claim 23, wherein
the image formation condition is a conveyance speed of the sheet or a fixing temperature for fixing a toner image onto the sheet or a voltage value for transferring a toner image onto the sheet.

* * * * *